US010711031B2

(12) United States Patent
Chernov et al.

(10) Patent No.: US 10,711,031 B2
(45) Date of Patent: Jul. 14, 2020

(54) METHOD FOR EXTRACTING PHYTOSTEROLS FROM TALL OIL PITCH

(71) Applicant: ORGKHIM BCH MANAGEMENT COMPANY, JSC, Nizhny Novgorod (RU)

(72) Inventors: Ilia Nikolaevich Chernov, Nizhegorodskaya obl. (RU); Alexey Olegovich Korshunov, Nizhegorodskaya (RU); Taras Ivanovich Dolinskiy, Nizhniy Novgorod (RU); Mikhail Alekseevich Lazarev, Nizhniy Novgorod (RU); Ekaterina Aleksandrovna Mavrina, Nizhegorodskaya obl. (RU); Ilia Sergeevich Ilichev, Nizhniy Novgorod (RU); Arkadiy Benyuminovich Radbil, Nizhniy Novgorod (RU)

(73) Assignee: ORGKHIM BCH MANAGEMENT COMPANY, JSC, Nizhny Novgorod (RU)

( * ) Notice: Subject to any disclaimer, the term of this patent is extended or adjusted under 35 U.S.C. 154(b) by 0 days.

(21) Appl. No.: 16/493,468

(22) PCT Filed: May 8, 2018

(86) PCT No.: PCT/RU2018/000296
§ 371 (c)(1),
(2) Date: Sep. 12, 2019

(87) PCT Pub. No.: WO2019/050430
PCT Pub. Date: Mar. 14, 2019

(65) Prior Publication Data
US 2020/0131221 A1    Apr. 30, 2020

(30) Foreign Application Priority Data

Sep. 11, 2017  (RU) ................ 2017131803

(51) Int. Cl.
*C07J 9/00* (2006.01)
(52) U.S. Cl.
CPC ...................... *C07J 9/00* (2013.01)

(58) Field of Classification Search
CPC .......................................................... C07J 9/00
See application file for complete search history.

(56) References Cited

U.S. PATENT DOCUMENTS

| 4,044,031 | A | * | 8/1977 | Johansson ............... C07J 9/00 |
| | | | | 552/545 |
| 4,849,112 | A | | 7/1989 | Barder et al. |
| 6,462,210 | B1 | | 10/2002 | Diaz |
| 2007/0231418 | A1 | | 10/2007 | Scheffler |

FOREIGN PATENT DOCUMENTS

| CN | 103923147 A | 7/2014 |
| JP | 2002194384 A | 7/2002 |
| RU | 2128662 C1 | 4/1999 |

OTHER PUBLICATIONS

ISR for International Application PCT/RU2018/000296.
Written Opinion for International Application PCT/RU2018/000296.
JP2002194384_Espacenet_English_Abstract.
RU 2128662 C1_Espacenet_English_Abstract.
English translation of first official action in Chinese Patent Application 201880017787.9 dated Dec. 31, 2019.
English abstract and machine translation of CN103923147A.

* cited by examiner

*Primary Examiner* — Paul A Zucker
(74) *Attorney, Agent, or Firm* — Ladas & Parry LLP

(57) ABSTRACT

A method for extracting phytosterols from tall oil pitch. The method involves saponifying tall oil pitch using an alkali in a polyatomic alcohol, extracting unsaponified matter from the alkali-alcohol solution using a hydrocarbon solvent, subsequently removing the solvent by distillation, and concentrating the phytosterols, wherein a mixture of paraffin hydrocarbons is used as said hydrocarbon solvent, and, following extraction from the extraction solution, betulin is isolated by crystallization and the phytosterols are then concentrated by means of rectification. This method enables an increase in the extraction rate of phytosterols from a saponified tall oil pitch up to 95%, producing the end product with phytosterol content of at least 65% with unwanted betulin impurities at no more than 0.3%.

5 Claims, No Drawings

METHOD FOR EXTRACTING PHYTOSTEROLS FROM TALL OIL PITCH

RELATED APPLICATION

This application is an application under 35 U.S.C. 371 of International Application No. PCT/RU2018/000296 filed on 8 May 2018 which claims priority from RU Application No. 2017131803 filed on 11 Sep. 2017, the disclosures of which are incorporated in their entirety by reference herein.

TECHNICAL FIELD OF INVENTION

The invention relates to the field of wood chemical industry and concerns a method for extracting phytosterols from tall oil pitch.

PRIOR ART

Phytosterols (other designations: phytosterins, plant sterols, plant sterins) relate to a group of sterols naturally present in plants. Phytosterols have a high biological activity and are used in animal feeds, in food, pharmaceutical, cosmetics and other industries.

The most promising area of phytosterol use is in preventive medication for controlling human blood cholesterol level and as food supplements for reducing the risk of cardiovascular diseases. It is evident that with the current trends of increased life expectancy and improved quality of life the problem of an efficient method for extracting phytosterols from plant raw materials is important.

One of the available raw materials rich in phytosterols and obtained from plant sources is tall oil pitch, which is a non-volatile fraction separated from raw tall oil during vacuum rectification. Considering that phytosterols derived from tall oil pitch are further used in food and pharmaceutical industries, methods, which allow achieving a high extraction rate with a low content of unwanted impurities, specifically of betulin, may be the most promising methods for extracting phytosterols.

There is a chromatographic method for extracting sterols from tall oil pitch (U.S. Pat. No. 4,849,112, published on 11 Dec. 1987) yielding 18.7%, which allows obtaining a high purity product (90% of β-sitosterol). However, the method requires complicated equipment and is also resource-consuming one because of the use of large amounts of adsorptive materials that can't be regenerated after being used.

There is a method for extracting phytosterols (sitosterols) by distillation (U.S. Pat. No. 6,462,210, published on 16 Apr. 1999). The method allows extracting a product with the content of sterols amounting up to 96%. However, this method requires multiple repetition of distillation steps which results in a decreased product yield and a high power consumption.

There is a method for producing sitosterol from coniferous wood tall oil pitch by saponification of the pitch with alkali, subsequent extraction with a gasoline-alcohol mixture and production of the target product (sitosterol) by crystallization after elimination of the extractant with ethyl acetate solution (RF Patent No. 2128662, published on 10 Apr. 1999). This method allows producing sitosterol for 4.5% of the weight of the initial raw material. However, the known method is not suitable to produce high quality phytosterols from a mixed wood tall oil pitch.

A method selected as a prototype, which is the closest to the claimed method in technical essence, is the method for extracting phytosterols from tall oil pitch described in application JP2002194384A. Said method consists in subjecting tall oil pitch to an alkaline hydrolysis in a polyatomic alcohol, then extracting unsaponifiable matters with a hydrocarbon solvent and separating phytosterols by crystallization. According to the known method hexane, or heptane, or toluene, or xylene is used as a hydrocarbon solvent for the extraction treatment of alkaline hydrolysis products. The known method is efficient and allows producing high purity sterols.

However, the method for producing phytosterols described in the prototype is efficient with the use of tall oil pitch originated from the wood of coniferous trees as initial raw material. The use of tall oil pitch originated from a mixed wood—coniferous and deciduous trees—in the known method does not allow achieving satisfactory results: the extract yield is 27.6% in comparison with the yield of 32% described in the prototype for a "coniferous" pitch, while the content of phytosterols in the extract is 24.6% in contrast to 52% described in the prototype. Hence, the extraction rate of sitosterol from a mixed wood tall oil pitch is 62.9% at the step of extracting according to the prototype, considering that the pitch comprises sterols only in the amount of 10 to 13%.

Moreover, the extract of unsaponifiable matters produced according to the known method with the use of tall oil pitch originated from mixed wood is found to contain about 2.1% of betulin derived from a deciduous wood. Betulin in the mixed wood pitch may amount to 5%, and is an unwanted component for a further sitosterol processing, so its content in sterols has to be minimal.

SUMMARY OF THE INVENTION

The problem of the present invention consists in the providing with a method for extracting phytosterols from tall oil pitch that allows producing phytosterol in high concentration with a low content of betulin.

A new technical result of the proposed method is the increase of the phytosterols extraction rate from saponified tall oil pitch to at least 95%, the production of an end product that has a phytosterol content of at least 65% with unwanted betulin impurities at no more than 0.3%.

The claimed technical result is achieved by the proposed method for extracting phytosterols from tall oil pitch, the method consists in saponifying tall oil pitch with an alkali in a polyatomic alcohol, extracting unsaponified matter from the alkali-alcohol solution using a hydrocarbon solvent, subsequently removing the solvent by distillation, and concentrating the phytosterols according to the invention, wherein a mixture of paraffin hydrocarbons with 8 to 17 carbon atoms is used as said hydrocarbon solvent, and, following the extraction betulin is isolated from the extract by crystallization at the temperature of 50 to 83° C. and the phytosterols are then concentrated by means of rectification.

Preferably, tall oil pitch comprises up to 3% betulin by weight.

Preferably, the crystallization of betulin is carried out at the temperature of 70 to 80° C.

Preferably, the extraction of unsaponifiable matters is carried out at the temperature of 100 to 135° C.

Preferably, a mixture of paraffin hydrocarbons with 10 to 13 carbon atoms is used as the hydrocarbon solvent.

The use of a mixture of paraffin hydrocarbons with 8 to 17 carbon atoms having a high boiling point allows increasing the extraction rate of unsaponified matters from the tall oil pitch due to the increased extraction temperature and solubilizing ability. At the same time, solvents having a higher solubilizing ability have a lower selectivity resulting in a simultaneous extraction of phytosterols and impurities, specifically of betulin. The latter has to be eliminated from the extract as an unwanted impurity.

It was experimentally determined that isolation of betulin from phytosterols is a challenging task, for said components have close boiling points. Experiments proved that a crystallization is the most efficient method for the isolation of betulin impurity from phytosterols. Considering that the solubility of betulin in paraffin hydrocarbons is less than that of phytosterols by an order of magnitude, the temperature of the extract solution is decreased to achieve maximal sedimentation of betulin crystals. Experiments evidence that the decrease of the temperature to less than 50° C. results in a betulin and phytosterol co-crystallization and in a significant loss of the target product, while the increase of the temperature of betulin crystallization above 83° C. is not expedient, for no improved efficiency of the process has been demonstrated. The range 70 to 80° C. was found to be the optimal temperature range for crystallization of a betulin impurity from the extract.

The solution obtained from the crystallization was rectified to achieve a near complete elimination of the impurity and to concentrate phytosterols.

DETAILED DESCRIPTION OF THE EMBODIMENTS

The claimed method is carried out in the following way.

Tall oil pitch is saponified at the temperature of 80 to 135° C. with an alkali dissolved in polyatomic alcohol.

The saponified tall oil pitch solution is extracted with a hydrocarbon solvent at the temperature of 100 to 135° C. Once the extraction and the separation of phases are completed, the raffinate solution comprising predominantly salts of resin and fatty acids dissolved in the polyatomic alcohol is removed from the bottom, while the extract solution of paraffin hydrocarbons comprising phytosterol neutral matters and impurities is collected from the top.

The temperature of the extract solution collected from the top is decreased and the betulin impurity is crystallized out. Then the solvent is removed by distillation under a reduced pressure and the distillation residue is fed to a rectifying column to concentrate the phytosterols.

INDUSTRIAL APPLICABILITY

Particular examples of the application of the claimed method are provided below.

Example 1

A reactor is fed with 40-50% aqueous alkali solution and ethylene glycol. The mixture is mixed and added with tall oil pitch preliminarily heated up to the temperature of about 90° C., with the ratio of ethylene glycol to tall oil pitch being respectively 1:1. The reaction mass is heated up to the temperature of 125 to 130° C. and mixed at this temperature for 3 to 5 hours.

The saponified tall oil pitch is extracted with a mixture of paraffin hydrocarbons $C_8$-$C_{10}$ in the same reactor at the temperature of 100° C. with the ratio of the saponified tall oil pitch to paraffin hydrocarbons of 1:2. Once being mixed, the mixture is left until the layers are completely separated, then the bottom layer is removed.

The temperature of the top layer—the extract solution—is reduced down to 70° C. and the betulin impurity is crystallized for 3 to 6 hours with weakmixing. The formed betulin crystals are filtered. The filtrate comprising phytosterols is distilled to remove the solvent and the distillation residue is fed to a rectifying column to concentrate the phytosterols.

The rectification is carried out on a glass column with the inner diameter of 20 mm having five theoretical plates under the residual pressure of 0.001 to 0.01 mbar. The temperature in the column still is 200° C., the temperature of the condenser is 70° C. The feed point of the column is in the middle.

The extraction rate of phytosterols was 95.3%. The end product contained 65% of phytosterols, the betulin impurity was 0.2%.

Example 2

The saponification of the tall oil pitch is carried out in a way similar to that of Example 1.

The saponified tall oil pitch is extracted with a mixture of paraffin hydrocarbons $C_{10}$-$C_{13}$ in the same reactor at the temperature of 135° C. with the ratio of the saponified tall oil pitch to extractant of 1:2. Once being mixed, the mixture is left until the layers are completely separated, then the bottom layer is removed.

The temperature of the top layer—the extract solution—is reduced to 65° C. and the betulin impurity is crystallized for 3 to 6 hours with weak mixing. The formed betulin crystals are filtered. The filtrate comprising phytosterols is fed to a rectifying column to concentrate the phytosterols.

The extraction rate of phytosterols was 96.5%. The end product contained 68% of phytosterols, the betulin impurity was 0.2%.

Example 3

The saponification is carried out in a way similar to that of Example 1.

The process is distinguished in that the saponification is carried out in a propylene glycol medium with the weight ratio of the tall oil pitch to propylene glycol of 1:2 and with the use of a mixture of paraffin hydrocarbons $C_{14}$-$C_{17}$ as an extractant at the extraction temperature of 130° C.

The rectification is carried out under the residual pressure of 0.001 mbar without reflux return. The other steps of the rectification process are identical to these of Example 1.

The extraction rate of phytosterols was 98%. The end product contained 69.5% of phytosterols, the betulin impurity was 0.1%.

Example 4

The saponification is carried out in a way similar to that of Example 1.

The process is distinguished in that the saponification is carried out in a propylene glycol medium with the weight ratio of the tall oil pitch to propylene glycol of 1:2 and with the use of a mixture of paraffin hydrocarbons $C_{14}$-$C_{17}$ as an extractant at the extraction temperature of 105° C. The crystallization of betulin is carried out at 80° C.

The reflux-to-product ratio during the rectification is 2. The other steps of the process are identical to those of Example 3.

The extraction rate of phytosterols was 96%. The end product contained 66.3% of phytosterols, the betulin impurity was 0.2%.

Example 5

The saponification is carried out in a way similar to that of Example 4.

The crystallization of betulin is carried out at 50° C.

The rectification is carried out on a glass column with the inner diameter of 20 mm having five theoretical plates under the residual pressure of 0.001 to 0.01 mbar. The temperature in the column still is 200° C., the temperature of the condenser is 70° C. The feed point of the column is in the middle.

The extraction rate of phytosterols was 95.8%. The end product contained 65% of phytosterols, the betulin impurity was 0.1%.

The results of the experiments carried out according to the proposed method and according to the prototype are provided in the Table.

| | | | Extraction conditions | | Extract | | | | End Product | |
|---|---|---|---|---|---|---|---|---|---|---|
| Example | Saponification condition | T saponification, ° C. | Extractant type | T extract, ° C. | Extract yield, % TOP | WF of phytosterol in extract, % | Phytosterol extraction rate from saponified TOP, % | WF of betulin in extract, % | WF of phytosterol, % | WF of betulin % |
| According to the prototype | TOP:PG = 1:1.5 | 160 | Hexane | 62 | 27.6 | 24.6 | 62.9 | 2.1 | — | — |
| 1 | TOP:EG = 1:1 | 125-130 | $C_8$-$C_{10}$ mixture | 100 | 28.8 | 25.2 | 95.3 | — | 65.0 | 0.2 |
| 2 | TOP:EG = 1:1 | 125-130 | $C_{10}$-$C_{13}$ mixture | 135 | 40.5 | 21.1 | 96.5 | — | 68.0 | 0.2 |
| 3 | TOP:PG = 1:2 | 125-130 | $C_{14}$-$C_{17}$ mixture | 130 | 35.8 | 35.1 | 98.0 | 2.4 | 69.5 | 0.1 |
| 4 | TOP:PG = 1:2 | 125-130 | $C_{14}$-$C_{17}$ mixture | 105 | 29.0 | 28.0 | 96.0 | — | 66.3 | 0.2 |
| 5 | TOP:PG = 1:2 | 125-130 | $C_4$-$C_{17}$ mixture | 105 | 28.5 | 27.8 | 95.8 | — | 65.0 | 0.1 |

TOP—tall oil pitch
EG—ethyleme glycol
PG—propylene glycol
WF—weight fraction

Consequently the proposed method allows increasing the extraction rate of phytosterols from a saponified tall oil pitch up to at least 95%, producing the end product with phytosterol content of at least 65% with unwanted betulin impurities at no more than 0.3%.

The invention claimed is:

1. A method for extracting phytosterols from tall oil pitch, the method consisting of saponifying tall oil pitch with an alkali in a polyatomic alcohol, extracting unsaponified matter from the alkali-alcohol solution using a hydrocarbon solvent, subsequently removing the solvent by distillation, and concentrating the phytosterols, wherein a mixture of paraffin hydrocarbons with 8 to 17 carbon atoms is used as the hydrocarbon solvent, and, following the extraction, botulin is isolated from the extract solution by crystallization at a temperature of 50 to 83° C. and the phytosterols are then concentrated by means of rectification.

2. The method according to claim 1, wherein the tall oil pitch comprises up to 3% betulin by weight.

3. The method according to claim 1, wherein the crystallization of betulin is carried out at a temperature of 70 to 80° C.

4. The method according to claim 1, wherein the extraction of unsaponifiable matters is carried out at a temperature of 100 to 135° C.

5. The method according to claim 1, wherein a mixture of paraffin hydrocarbons with 10 to 13 carbon atoms is used as the hydrocarbon solvent.

* * * * *